US005703228A

United States Patent [19]
Heidlas et al.

[11] Patent Number: 5,703,228
[45] Date of Patent: Dec. 30, 1997

[54] PROCESS FOR THE PURIFICATION OF CARBOHYDRATE DERIVATIVES WITH SURFACE-ACTIVE PROPERTIES

[75] Inventors: Jürgen Heidlas, Trostberg; Jan Cully, Garching, both of Germany

[73] Assignee: SKW Trostberg Aktiengesellschaft, Trostberg, Germany

[21] Appl. No.: 598,348

[22] Filed: Feb. 8, 1996

[30] Foreign Application Priority Data

Feb. 8, 1995 [DE] Germany ............ 195 04 101.1

[51] Int. Cl.$^6$ ................ C07H 1/06; C07H 1/00
[52] U.S. Cl. ........................... 536/127; 536/124
[58] Field of Search ....................... 536/127, 124

[56] References Cited

U.S. PATENT DOCUMENTS

| | | | |
|---|---|---|---|
| 2,548,434 | 4/1951 | Leader | 554/16 |
| 2,682,551 | 6/1954 | Miller | 554/20 |
| 5,405,633 | 4/1995 | Heidlas et al. | 426/442 |
| 5,466,842 | 11/1995 | Heidlas et al. | 554/83 |

FOREIGN PATENT DOCUMENTS

| | | |
|---|---|---|
| 2118894 | 9/1994 | Canada . |
| 0591981 | 4/1994 | European Pat. Off. . |
| 0615694 | 9/1994 | European Pat. Off. . |
| 0616025 | 9/1994 | European Pat. Off. . |

OTHER PUBLICATIONS

Siegfried et al, Angewandte Chemie (1978), 90(10), "Trennung Schwerfluch–Tiger Stoffe mit Komprimierten Gasen in Gegenstromkolonnch", pp. 794–798.

*Primary Examiner*—John Kight
*Assistant Examiner*—Everett White
*Attorney, Agent, or Firm*—Felfe & Lynch

[57] ABSTRACT

A process is described for the purification of carbohydrate derivatives with surface-active properties in which an extraction process is used to liberate the solid or liquid starting material from undesired lipophilic by-products by the use of compressed propane or a proportionate mixture thereof with butane at pressures between 8 and 150 bar and a process temperature below 120° C. In this way it is possible to isolate valuable raw materials in a gentle manner either batch-wise or continuously which meet the high purity requirements, for example in the field of cosmetics.

14 Claims, No Drawings

PROCESS FOR THE PURIFICATION OF CARBOHYDRATE DERIVATIVES WITH SURFACE-ACTIVE PROPERTIES

BACKGROUND OF THE INVENTION

The present invention concerns a process for the purification of carbohydrate derivatives with surface-active properties by using compressed gases.

Carbohydrates have recently gained an increasing importance within the field of well priced renewable raw materials in the chemical industry. Synthetic surface-active carbohydrate compounds, so-called surfactants, in which the hydrophilic carbohydrate structures of monosaccharides, disaccharides or oligosaccharides are connected with the lipophilic structure of hydrophobic hydrocarbon chains e.g. long alkyl or alkylene chains are outstanding examples. Although, there are several possibilities for a chemical linkage between carbohydrates and hydrocarbon chains such as e.g. ester, ether, amide or amino functions, mainly carbohydrate esters (sugar esters) and alkyl glycosides (1-O-sugar ethers) or combinations thereof, e.g. esterified alkyl glycosides, have predominated in industrial production. Apart from the very good surface-active effects, these products are particularly characterized by their straight biodegradability. As a result of their good skin tolerance, they are often used in the field of cosmetics.

In the production of sugar esters the corresponding carbohydrates, e.g. glucose or sucrose, are reacted with acylating reagents such as fatty acid derivatives (e.g. fatty acid methyl esters or glycerides) by esterification or transesterification until the desired degree of acylation is achieved. However, the acylation does not proceed to a uniform product, but to a variety of reaction products composed of mono-, di- or multi acylated sugars and varying amounts of the non-reacted starting materials.

Surface-active alkyl glycosides are usually obtained by reacting sugars with an excess of fatty alcohols. Consequently, the products are mixtures that still contain large amounts of non-reacted fatty alcohol.

Although the aforementioned reaction products already present good surface-active properties, further purification is desired for certain applications which aim to separate the by-products, such as non-reacted fatty acids, fatty acid methyl esters, glycerides or fatty alcohols.

Distillation processes and conventional solvent processes are known among others from the state of the art for this separation purpose which, however, have considerable disadvantages. In distillation processes one has to take into account the significant temperature sensitivity of the carbohydrate derived products. In general carbohydrate derivatives are very susceptible to caramelization leading to degradation and formation of dark colored products. Furthermore, it is known that thermal stress may induce a disproportionation effecting a change of the composition of the reaction products during the distillation process. In addition the products have a difficult to control tendency to foam during distillation. On the other hand solvent processes in general provide the crucial disadvantage that the desired surface-active action of the target products is a severe technical impediment to the efficient separation of the product mixtures since the formation of emulsions effects phase separation.

Numerous processes are known from the literature which describe the extraction of lipophilic substances with compressed gases. Above all compressed hydrocarbons have already been used for a long time as media for the extraction of fats and oils.

Thus a selective process for the extraction and fractionation of fat-like materials is known from the U.S. Pat. No. 2,548,434 in which colorless fats are obtained with the aid of liquefied hydrocarbons such as propane, butane etc. or mixtures thereof at temperatures between 66° and 93.3° C. from wholemeal, rinds and bleaching earth and separated from the undesired dark-colored components.

A further process for the liquid extraction of oil-containing materials such as oil seeds, rinds, fish meal etc. with the aid of liquefied hydrocarbons such as propane is described by the U.S. Pat. No. 2,682,551.

The purification of carbohydrates by extraction with compressed gases or gas mixtures has not previously been known. In particular, none of the described processes is suitable for purifying synthetic carbohydrate derivatives from undesired by-products in an economic and straightforward manner and without several process steps.

Therefore the object of the present invention was to develop a process for purifying carbohydrate derivatives with surface-active properties which circumvents the disadvantages of the aforementioned technologies of the state of the art but enables carbohydrate derivatives of high purity to be provided in a sophisticated manner, especially that is regarding the thermal sensitivity of the desired products.

THE INVENTION

The above stated object is obtained according to the invention in that a starting material containing the carbohydrate derivatives and impurities is extracted with compressed propane or mixtures thereof containing up to 25% by weight butane at pressures between 8 and 150 bar, in particular between 20 and 80 bar and at temperatures of <120° C. during which the desired carbohydrate derivates are separated from impurities and by-products.

Surprisingly, the compressed propane and mixtures thereof containing butane in a liquid and near critical state are very well suited for separating reaction products such as fatty acids, fatty acid esters, glycerides or fatty alcohols from a reaction mixture which is formed during the production of sugar esters or alkyl glycosides. In this connection it was found that the impurities present in the reaction mixture have a higher solubility than the carbohydrate derivatives and can be separated without severe formation of emulsions.

The extraction can be carried out either with solid or liquid (liquefied) starting materials. Whereas solid starting materials can generally be purified batch-wise by a solid/liquid extraction technique, in the case of liquid (liquefied) starting materials a continuous liquid/liquid extraction can be carried out; then the process is preferably carried out in a separation column preferably in the counter-current mode. In this process the extraction medium is fed in against the flow of mixture of the starting material to be separated during which the sugar derivatives (esters, alkyl glycosides) do not dissolve in the extraction medium or only very poorly and accumulate in the bottom product of the column. The impurities and by-products such as fatty acids, fatty acid esters, glycerides or fatty alcohols that need to be separated are very readily soluble in the compressed gas (mixture) under the conditions according to the invention and are transferred from the column together with the extraction medium as a so-called top product. The separation efficiency in the column can be improved by heating the extraction column with a temperature gradient of $\Delta T \leq 20°$ C. in which case the higher temperature is without exception always at the top of the column and the upper temperature limit at the top is the maximum process temperature of 120° C.

In principle it is also possible to use higher process temperatures than those according to the invention, but these are not recommended due to the described temperature sensitivity of the products since decomposition reactions occur. The lower limit for the process temperature is given by the respective process pressure and by quite general aspects of economic efficiency.

The compressed gases used or mixtures thereof always have a very good solubilizing power for the impurities to be separated independent of the mixture to be separated so that the process is distinguished by very good space-time yields. In the described process 3 to 15 grams of compressed gas (mixture) are typically required per gram of the mixture to be separated.

A surprising advantage of the process according to the invention is also that the compressed extraction gas (mixture) at least partially dissolves in the materials to be separated and thus lowers high viscosities. This lowering of the viscosity enables the effective extraction of the said mixtures since the limiting mass transfer at the phase interface is considerably improved.

The separation of the purified products from the extraction medium is straight forward and can for example be achieved by lowering the pressure and/or increasing the temperature effecting an evaporation of the extraction solvent and, consequently, the precipitation of the extracted materials.

The extraction medium can subsequently be recovered by recompression and/or liquefaction and recycled to the extraction process.

The process is particularly advantageous when the purified carbohydrate derivatives accumulate as solid products. Due to the fact that the compressed gas (mixture) dissolves in the product under pressure and as a result keeps it in a melt (at moderate temperatures), the product can be transferred from the bottom of the column through a suitable nozzle device during which the gas (mixture) on the one hand vapourizes spontaneously after depressurization and on the other hand the pure product accumulates as a fine powder.

It is intended to elucidate the process according to the invention by the following examples.

EXAMPLE 1

Purification of a mixture of methyl glycoside esters of oleic, stearic, linoleic and palmitic acid from the corresponding free fatty acids A reaction mixture from the production of methyl glycoside esters of oleic, stearic, linoleic and palmitic acid (the sum of the monoesters and higher esters being together 75% by weight) was contaminated with 16% by weight of the corresponding free fatty acids. The starting material was melted at 55° C. and was fed in a proportion of 10% by weight into the ascending compressed propane at 50 bar and 85° C. in a countercurrent manner in a high pressure extraction column (column volumes 21, height 2 m). Due to their poorer solubility, the polar carbohydrate derivatives mainly accumulate at the bottom of the column whereas the free fatty acids are led out of the top of the column together with the extraction medium. The top product which mainly contains the free fatty acids was transferred into a separator in which the extracted compounds were precipitated by vapourizing the liquid propane at 10 bar and 60° C. The extraction gas was subsequently re-liquefied and again fed into the extraction process. The bottom product (80% by weight in relation to the amount fed in) was expanded directly from the column to atmospheric pressure by means of a suitable discharging device to yield the purified methyl glycoside esters (in total 91% by weight as a sum of the monoesters and higher esters, 6% by weight free fatty acids).

EXAMPLE 2

Purification of a mixture of methyl glycoside esters of isostearic acid from the corresponding free isostearic acid.

A reaction mixture from the production of methyl glycoside esters of isostearic acid (the sum of the monoesters and higher esters being together 71% by weight) was contaminated with 21% by weight of the corresponding free fatty acids. The starting material, melted at 55° C., was countercurrently fed in a proportion of 15% by weight into the ascending compressed propane at 80 bar and 95° C. in a high pressure extraction column (column volumes 21, height 2 m). Due to their poorer solubility, the polar carbohydrate derivatives mainly accumulate at the bottom of the column whereas the free fatty acids are led to the top of the column together with the extraction medium. The top product which mainly contains the free fatty acids was transferred into a separator in which the extracted compounds were precipitated by vaporizing the liquid propane at 10 bar and 60° C. The extraction gas was subsequently liquefied and reused for the extraction process. The bottom product (73% by weight in relation to the amount fed in) was expanded directly from the column to atmospheric pressure by means of a suitable discharging device to yield the purified methyl glycoside esters (in total 85% by weight as a sum of the monoesters and higher esters, 6% by weight free fatty acids).

EXAMPLE 3

Purification of a mixture of alkyl polyglycosides (mono-, di-, trisaccharides) and corresponding free fatty alcohols with a chain length of $C_{12}$ to $C_{18}$.

A reaction mixture from the production of alkyl polyglycosides (mixtures of mono-, di-, trisaccharides, 25% by weight) was contaminated with 70% by weight of the corresponding free fatty alcohols with a chain length of $C_{12}$ to $C_{18}$. The melted starting material that was fed in a proportion of 15% by weight countercurrent into the ascending compressed propane at 80 bar and 85° C. in a high pressure extraction column (column volumes 21, height 2 m). Due to their poorer solubility, the polar carbohydrate derivatives mainly accumulate at the bottom of the column whereas the fatty alcohols are led out of the top of the column together with the extraction medium. The top product which mainly contains the fatty alcohols was transferred into a separator in which the extracted compounds were precipitated by vaporizing the liquid propane at 10 bar and 60° C. The extraction gas was subsequently liquefied and fed into the extraction process for the subsequent extraction cycle. The bottom product (20% by weight in relation to the amount fed in) was removed directly from the column to atmospheric pressure by means of a suitable discharging device to yield the purified alkyl polyglycosides in powder form (purity>90 by weight, fatty alcohols<5% by weight).

It will be understood that the specification and examples are illustrative but not limitative of the present invention and that other embodiments in the spirit and scope of the invention will suggest themselves to those skilled in the art.

We claim:

1. A process for the purification of a carbohydrate derivative with surface-active properties, comprising: extracting a starting material containing the carbohydrate derivative and impurities with an extraction medium comprising compressed propane or mixtures thereof containing up to 25% by weight butane at pressures between 8 and 150 bar and a temperature of less than 120° C. whereby the impurities are separated from the carbohydrate derivative.

2. The process of claim 1 wherein the pressure is between 20 and 80 bar.

3. The process of claim 1, wherein the impurities have a higher solubility in the extraction medium than the carbohydrate derivatives.

4. The process of claim 1, wherein the starting material is solid and is subjected batch-wise to a solid/liquid extraction.

5. The process of claim 1, wherein the starting material is liquid (liquified) and is subjected to a liquid/liquid extraction.

6. The process of claim 5, wherein the extraction is carried out in a countercurrent manner.

7. The process of claim 5, wherein the extraction is carried out in a separation column with a temperature gradient of $\Delta T$ less than or equal to 20° C. that increases towards the top of the column.

8. The process of claim 1, wherein 3 to 15 grams of compressed gas (mixture) is used per gram of starting material to be extracted.

9. The process of claim 1, wherein the carbohydrate derivative is obtained by reducing the pressure and/or increasing the temperature during which the extraction medium is converted into a gaseous state.

10. The process of claim 1, wherein the extraction medium is recycled.

11. The process of claim 1, wherein the carbohydrate derivatives are selected from mono-, di- and/or oligosaccharidic carbohydrates having lipophilic groups.

12. The process of claim 11, wherein the carbohydrate derivatives are carbohydrate esters, carbohydrate ethers, esterified carbohydrate ethers or mixtures thereof.

13. The process of claim 1, wherein lipophilic substances are separated as impurities.

14. The process of claim 13 wherein the lipophilic substances comprise at least one of fatty acids, fatty acid esters, glycerides and fatty alcohols.

* * * * *